(12) United States Patent
Gayet

(10) Patent No.: US 10,857,242 B2
(45) Date of Patent: Dec. 8, 2020

(54) MULTIVALENT TARGETING FLUORESCENT TRACER IN THE NEAR INFRARED RANGE FOR OPTICAL IMAGING

(71) Applicant: FLUOPTICS, Grenoble (FR)

(72) Inventor: Pascal Gayet, Grenoble (FR)

(73) Assignee: FLUOPTICS, Grenoble (FR)

( * ) Notice: Subject to any disclaimer, the term of this patent is extended or adjusted under 35 U.S.C. 154(b) by 0 days.

(21) Appl. No.: 15/576,254

(22) PCT Filed: May 24, 2016

(86) PCT No.: PCT/EP2016/061711
§ 371 (c)(1),
(2) Date: Nov. 21, 2017

(87) PCT Pub. No.: WO2016/189004
PCT Pub. Date: Dec. 1, 2016

(65) Prior Publication Data
US 2018/0147303 A1    May 31, 2018

(30) Foreign Application Priority Data
May 25, 2015    (FR) .................... 15 54668

(51) Int. Cl.
*C07K 7/50* (2006.01)
*A61K 49/00* (2006.01)

(52) U.S. Cl.
CPC ...... *A61K 49/0056* (2013.01); *A61K 49/0032* (2013.01); *C07K 7/50* (2013.01)

(58) Field of Classification Search
CPC ............ A61K 49/0056; A61K 49/0032; C07K 2319/33; C07K 7/64
See application file for complete search history.

(56) References Cited

U.S. PATENT DOCUMENTS

| 7,531,622 B2 * | 5/2009 | Dumy ...................... C07K 7/64 530/317 |
| 2014/0271482 A1 * | 9/2014 | Low ................... G01N 33/6893 424/9.6 |
| 2014/0275533 A1 | 9/2014 | Kularatne et al. |

FOREIGN PATENT DOCUMENTS

WO    2004/026894 A3    4/2004

OTHER PUBLICATIONS

E. Garanger: "Conception, Synthese et Caracterisation de Nouveaux Systemes de Guidage et de Vectorisation pour la Cancerologie," Thesis, University Joesph Fourier, Grenoble 1, Jul. 26, 2005, XP055262866.
H. Hyun et al., "c-GMP-compatible preparative scale of near-infrared fluorophores," Contrast Media Mol. Imaging, vol. 7, No. 6, 2012, pp. 516-524.
P. Dumy et al., "A Convenient Synthesis of Cyclic Peptides as Regioselectively Addressable Functionalized Templates (RAFT)," Tetrahedron Letters, vol. 36, No. 8, 1995, pp. 1255-1258.
Didier Boturyn et al., "Template Assembled Cyclopeptides as Multimeric System for Integrin Targeting and Endocytosis," Journal of the American Chemical Society, 2004, vol. 126, No. 18. pp. 5730-5739.

* cited by examiner

*Primary Examiner* — Sudhakar Katakam
(74) *Attorney, Agent, or Firm* — BakerHostetler

(57) ABSTRACT

A fluorescent tracer for targeting tumors, comprises: at least one first fluorophore fluorescing in a range of wavelengths of between 700 and 1000 nm, a targeting assembly comprising at least two identical targeting molecules, and a cyclic oligopeptide: configured so as to define a mean plane defining a first upper face and a second lower face, comprising at least one first lysine amino acid residue on the second lower face, the targeting molecules being fixed to the first upper face of the mean plane, the fluorophore being fixed to the second lower face of the mean plane via a spacer arm connecting a carbon of the sequence of the at least three double bonds and the lysine amino acid residue of the oligopeptide.

Figure 1:
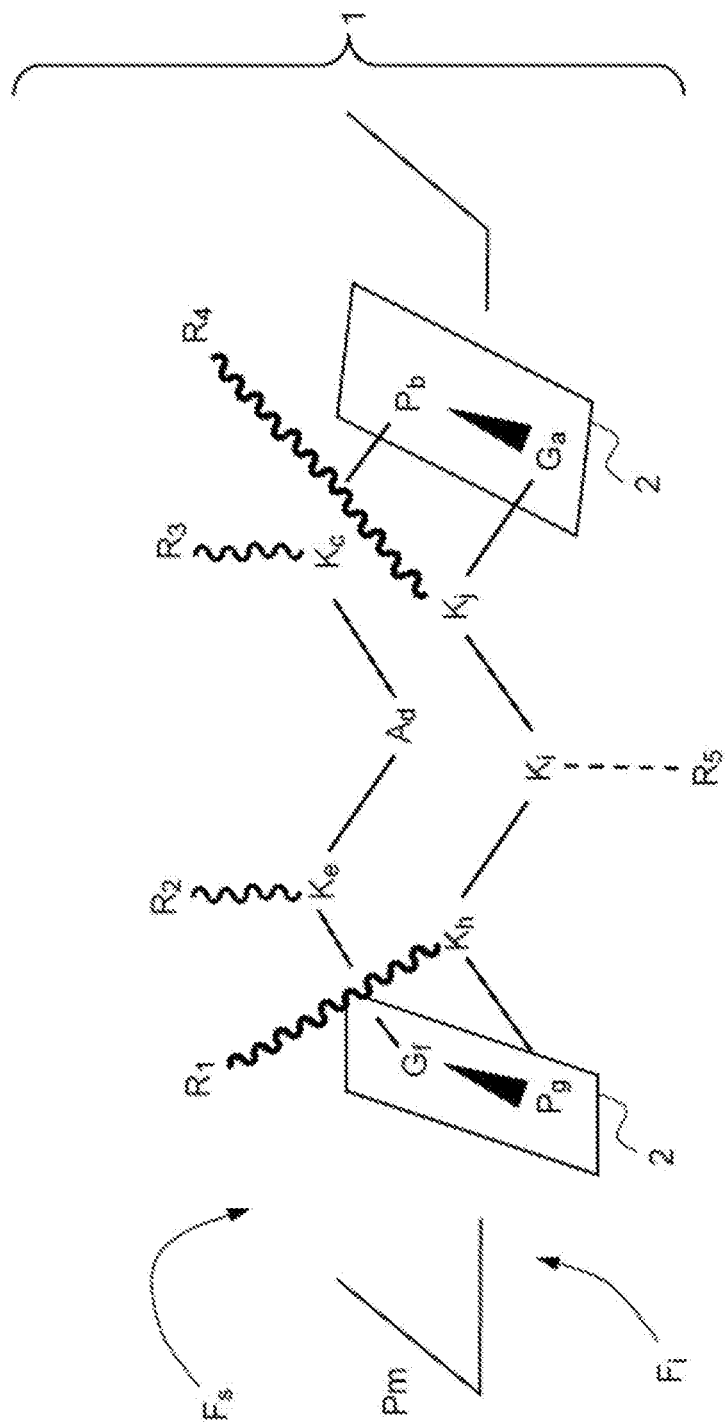

2 Claims, 16 Drawing Sheets

MULTIVALENT TARGETING FLUORESCENT TRACER IN THE NEAR INFRARED RANGE FOR OPTICAL IMAGING

CROSS-REFERENCE TO RELATED APPLICATIONS

This application is a National Stage of International patent application PCT/EP2016/061711, filed on May 24, 2016, which claims priority to foreign French patent application No. FR 1554668, filed on May 25, 2015, the disclosures of which are incorporated by reference in their entirety.

FIELD OF THE INVENTION

The present invention relates to compounds such as probes with fluorescence in the near-infrared range. These compounds comprise targeting molecules for target tissues or organs, a fluorophore and a support on which the targeting molecules and the fluorophore are fixed.

TECHNOLOGICAL BACKGROUND

Fluorescence imaging is growing rapidly in numerous surgical applications. Several medical devices are available on the market which enable the detection and visualization of one of the only fluorophores which has marketing authorization, indocyanine green. However, this fluorophore is a molecule which is not specific for target tissues or organs, which restricts the field of use thereof.

Medical imaging is a promising technique in surgical procedures. It may, for example, serve to guide the surgeon during surgery. This technique relies on the administration of a fluorescent tracer to the patient. In the case in point, this is a fluorescent tracer which targets the tissues or organs requiring the surgical procedure.

The principle is based on illumination, by a light source, of a fluorescent tracer, administered to the patient beforehand, which is specific for target tissues or organs. The illumination has the effect of exciting said fluorescent tracer, which then in turn emits radiation at a given wavelength. The main applications are in the near-infrared range, between 700 nm and 1000 nm. This is because this optical window corresponds to the range of wavelengths in which biological tissues absorb the least.

The advantage of fluorescent tracers is that they make it possible to combine properties of at least two classes of molecules, such as the properties of fluorescence on the one hand and the properties of targeting specific tissues or organs on the other.

The American patent applications US20140271482 by Low and US 20140275533 by Kularatne especially present monovalent fluorescent molecules targeting specific tissues. A molecule is said to be monovalent when it only fixes one example of a targeting molecule. In the case in point, the probes described target zones associated with inflammatory diseases. These applications do not disclose a multivalent support enabling the fixing of several targeting molecules, for example.

The aim of the present invention is to propose a molecule or tracer targeting specific tissues or organs. More specifically, the aim of the present invention is to propose a fluorescent tracer comprising a multivalent fluorescent support having anchor points for targeting molecules.

With this in mind, patent EP1539804 by P. Dumy describes a process for synthesizing a peptide support or molecular template.

FIG. 1 represents an example of a molecular template. This is a molecular template 1, better known under the name RAFT, an acronym standing for "regioselectively addressable functionalized template".

It is a cyclic decapeptide comprising the sequence of amino acid residues: [Glycine$_a$-Proline$_b$-Lysine$_c$-Alanine$_d$-Lysine$_e$-Glycine$_f$-Proline$_g$-Lysine$_h$-Lysine$_i$-Lysine$_j$-], the sequences of the amino acids [-Glycine$_{a;}$ $_f$-Proline$_{b;}$ $_g$-] forming bends 2 such that the configuration of the molecular template 1 has a mean plane Pm defining what is referred to as an upper face F$_s$ comprising four lysine residues K$_c$, K$_e$, K$_h$ and K$_j$ of the cyclic decapeptide and what is referred to as a lower face F$_i$, opposite to the upper face F$_s$, comprising at least one lysine K$_i$.

Mean plane Pm is intended to mean the plane for which the sum of the distances between the mean plane Pm and the amino acid residues is minimal.

The preparation of the molecular template 1 comprises a first step of synthesizing the linear decapeptide, the elongation method used in order to obtain the linear decapeptide starting from a glycine anchored in a resin being described in the prior art "P. Dumy et al. *Tetrahedron Lett.* 1995, 36, 1255-1258", a second step of intramolecular cyclization of the linear decapeptide so as to obtain a cyclic molecular template, and a third step of functionalization of the cyclic molecular template 1 according to the desired functionalities.

The RAFT cyclic decapeptide produced in this way is multivalent; it may be associated in a controlled manner with two independent functional domains: one domain intended for targeting zones of interest, such as zones expressing integrins, and one domain for detection.

"Integrins" are intended to mean the transmembrane heterodimers of cell surface receptors which have a role in processes of cell-cell and cell-extracellular matrix adhesion. Integrins have an important role in the attachment of cells to their environment, and in particular to the network of proteins of the extracellular matrix. The $\alpha_v\beta_3$ integrin is an integrin identified as being specific for zones of angiogenesis. It has been demonstrated that this integrin was overexpressed by the endothelial cells of neoangiogenic vessels; it has also been demonstrated on numerous human tumor cell lines.

Numerous integrins interact with their protein substrates via the sequence of amino acid residues -RGD-, the acronym for "arginine-glycine-aspartic acid". This RGD sequence is a common motif present on the majority of the proteins of the extracellular matrix.

Figure 2:
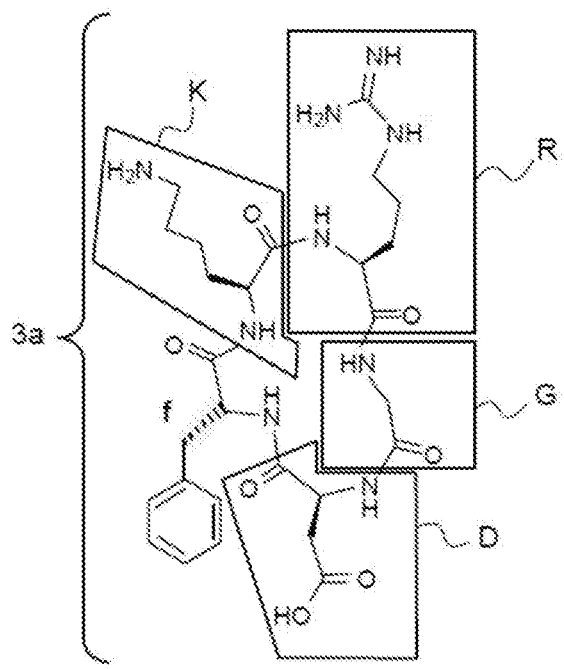

FIG. 2 presents the chemical formula of a targeting molecule 3 comprising a cyclic pentapeptide specific for the $\alpha_v\beta_3$ integrin comprising the sequence of amino acid residues R, G and D, the acronym for arginine, glycine, aspartic acid [-RGDfK-].

These observations have therefore served as the basis for developing molecules for the specific targeting of the $\alpha_v\beta_3$ integrin.

A publication by Boturyn et al. *"Template Assembled Cyclopeptides as Multimeric System for Integrin Targeting and Endocytosis"*, J. Am. Chem. Soc. 2004, 126, 5730-5739, also presents fluorescent tracers specific for the $\alpha_v\beta_3$ integrin. Boturyn's tracer comprises a RAFT template configured so as to define a mean plane, as defined in the abovementioned patent by P. Dumy, enabling the fixing of targeting molecules on one side of the mean plane and, on the other side of the mean plane, the fixing of the fluorophore directly to a lysine residue of what is referred to as the lower face of the RAFT template. In the case in point, the targeting molecules comprise four cyclopentapeptides comprising the peptide sequence RGD. The fluorophore is fluorescein which fluoresces in the visible range of wavelengths.

Figure 3:
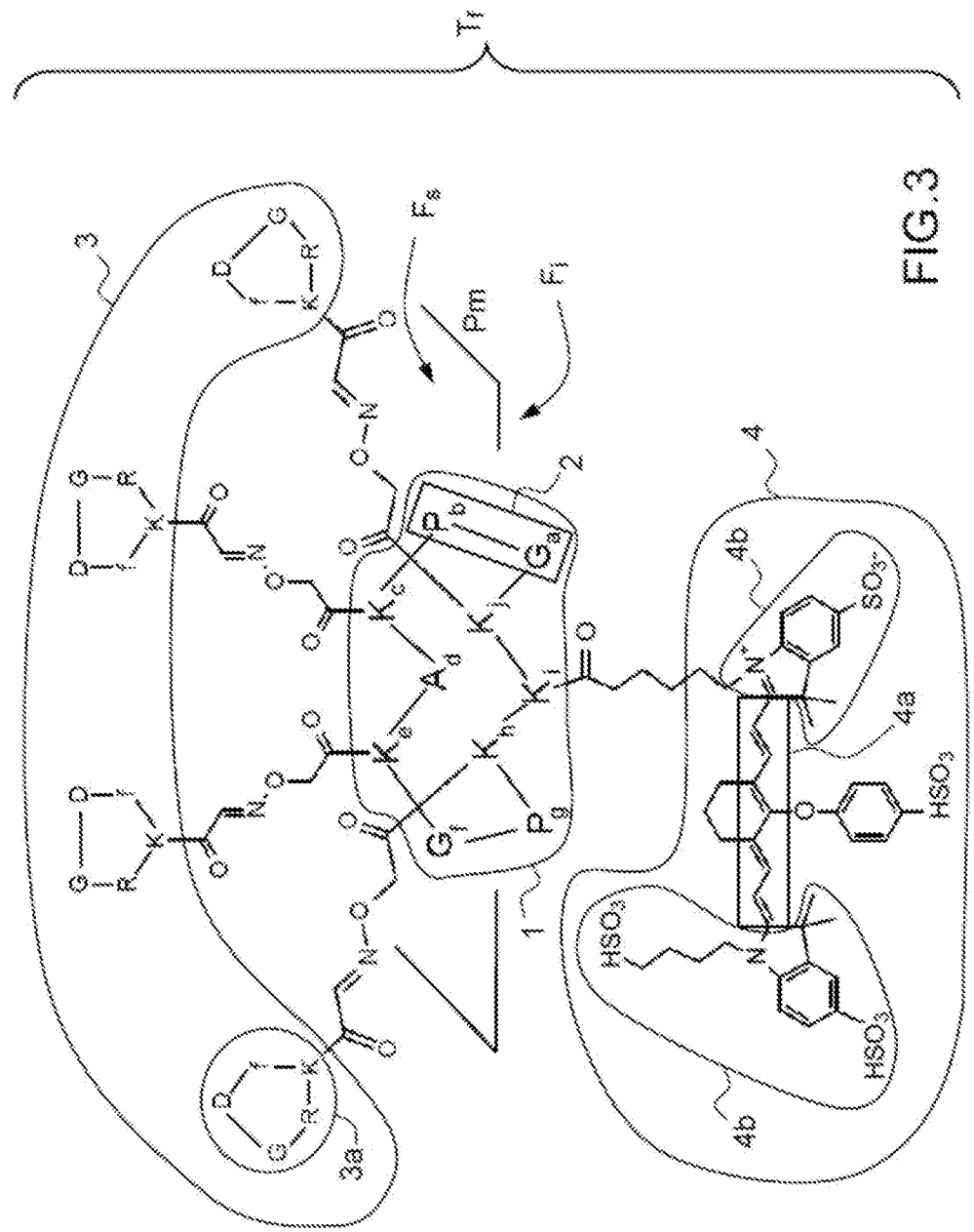

On the basis of these developments, a tracer, represented in FIG. 3, which is fluorescent in the near-infrared range and is specific for the $\alpha_v\beta_3$ integrin has been proposed.

The fluorescent tracer Tf comprises:
a molecular template 1, in the case in point the RAFT cyclic decapeptide comprising the sequence of ten amino acid residues: [-$G_a$-$P_b$-$K_c$-$A_d$-$K_e$-$G_f$-$P_g$-$K_h$-$K_i$-$K_j$] described in FIG. 1,
a fluorophore 4 of the family of cyanines fluorescing in the range of wavelengths of between 700 and 900 nm, and
an assembly 3 for targeting the $\alpha_v\beta_3$ integrin. In the case in point, the targeting assembly 3 comprises four targeting molecules 3a comprising the cyclopentapeptide comprising the sequence of amino acid residues [-RGD-].

The cyclopentapeptide molecules 3 are coupled to the four lysine amino acid residues $K_c$, $K_e$, $K_h$ and $K_j$ of what is referred to as the upper face $F_s$ of the molecular template 1 via oxime bonds.

The fluorophore 4 especially comprises a carbon-based chain 4a having covalent double bonds and an indole aromatic group 4b at the ends of the carbon-based chain 4a arranged so as to enable delocalization of the electrons of the double bonds over the whole of the carbon-based chain 4a and the indole aromatic groups 4b.

It should be noted that here the fluorophore 4 is IRDye800 (registered trademark), but it may also be cyanine 5 (registered trademark), Alexa fluor 700 (registered trademark) or a fluorophore developed specifically at 700 nm, denoted BM 105 (registered trademark).

The fluorophore 4 is linked to a lysine residue $K_i$ of what is referred to as the lower face $F_i$ of the molecular template 1 by forming an amide bond via an aliphatic group of one of the aromatic indole groups 4b.

The process for producing the fluorescent tracer Tf according to the prior art comprises:
a first step of synthesizing the RAFT template 1 comprising:
a sub-step of synthesizing a linear decapeptide on resin [-K(boc)-K(Alloc)-K(Boc)-P-G-K(Boc)-A-K(Boc)-P-G],
a sub-step of cyclizing the decapeptide in solution,
a sub-step of deprotecting the K(Boc)s,
a sub-step of grafting a protected oxyamine precursor,
a sub-step of deprotecting K(Alloc).
a second step of synthesizing the targeting molecule 3, in this case the cyclic pentapeptide [-D(tBu)-f-K(Alloc)-R(Pbf)-G-] 3a,
a third step of coupling between the RAFT template 1 and targeting molecules 3a, comprising:
a sub-step of cyclizing the pentapeptide in solution,
a sub-step of deprotecting K(Alloc),
a sub-step of grafting protected S,
a sub-step of deprotecting D, S and R, and
a sub-step of oxidizing S,
a fourth step of activating the fluorophore 4. In practice, the fluorophore is sold in the activated form, which makes it particularly unstable and reactive with regard to amines.
a fifth step of coupling, subsequent to the third and fourth steps, between the RAFT template comprising the targeting molecule 3a RAFT[-RGD-] and the fluorophore 4.

The yields of this process are relatively low; especially the yield from coupling between the RAFT template 1 comprising the targeting molecules and the fluorophore 4.

Indeed, to obtain 15 g of fluorescent tracer Tf such as that described in FIG. 3, 410 g of targeting molecule 3a, 75 g of RAFT template 1 and 7 g of fluorophore 4 are necessary.

The overall costs of producing a fluorescent tracer Tf according to the known art are very high, due both to the cost of purchasing the fluorophore 4 and also to the synthesis process which generates high losses of starting materials.

SUMMARY OF THE INVENTION

Thus, an aim of the invention is to propose a targeting fluorescent tracer having a cost very much lower than that of a fluorescent tracer according to the known art.

According to one aspect of the invention, a fluorescent tracer for targeting tumors is proposed, comprising:
at least one first fluorophore, an emission peak of which is between 770 nm and 870 nm, comprising a linear carbon-based chain comprising at least one sequence of at least three covalent carbon-carbon double bonds, so as to enable delocalization of the electrons of the double bonds when the fluorophore is excited by light radiation so as to fluoresce,
an assembly for targeting integrin comprising at least two identical targeting molecules, and
a cyclic oligopeptide:
configured so as to define a mean plane defining a first upper face and a second lower face,
comprising at least one first lysine amino acid residue on the second lower face,
targeting molecules being fixed to the first upper face of the mean plane,
the fluorophore being fixed to the second lower face of the mean plane via a spacer arm connecting a carbon of the sequence of the at least three double bonds and the lysine amino acid residue of the oligopeptide.

The fluorescent tracer according to the invention especially makes it possible to use less expensive commercial fluorophores than those used in the process of the prior art.

Advantageously, said spacer arm is able to increase delocalization of the electrons of said carbon-based chain.

Advantageously, the oligopeptide is a decapeptide. Thus, the fluorescent tracer is readily eliminated, which limits the toxicity thereof for the body.

Advantageously, the first face and the second face of the decapeptide are chemoselectively functionalizable.

Preferentially, the decapeptide comprises the following sequence of amino acid residues: [K-K-K-P-G-K-A-K-P-G-].

Advantageously, the spacer arm comprises a linear carbon-based chain comprising a number of carbons greater than or equal to four, thereby making it possible to limit the problem of steric hindrance or spacing during coupling between the fluorophore and the template.

Advantageously, the spacer arm is connected to the fluorophore via a bond chosen from an amide, ether or thioether bond.

Advantageously, the spacer arm is connected to the oligopeptide via an amide bond.

Advantageously, the fluorophore is from the cyanine family, and the fluorophore is preferentially chosen from the following fluorophores: S0121, S0306, S0456, S2180, IR775 chloride, IR780 iodide, IR786, IR806, IR820.

Advantageously, the oligopeptide comprises a second lysine residue on the lower face; a second fluorophore is attached to said lysine residue via a spacer arm, or not. The two fluorophores may then interact so as to enable FRET fluorescence, FRET being the acronym for "Förster resonance energy transfer", or energy transfer between fluorescent molecules.

Advantageously, the targeting molecules comprise a peptide or pseudo-peptide. Also, preferentially, the targeting molecules comprise cyclic pentapeptides and the peptide sequence of the pentapeptide targeting an integrin comprises the amino acid residues [-arginine-glycine-aspartic acid-] (RGD).

Advantageously, the oligopeptide comprises lysine residues on the upper face, to which the targeting molecules are fixed via an oxime bond. This type of bond gives the fluorescent tracer good in vivo and in vitro stability.

Alternatively, the targeting molecules are fixed via amide bonds.

Alternatively, the oligopeptide comprises at least one cysteine residue on the first upper face, to which a targeting molecule is fixed via a thioether bond, enabling regioselective fixing of different targeting molecules.

According to another aspect of the invention, a process for synthesizing a fluorescent tracer for targeting tumors is proposed, comprising:
- at least one first fluorophore comprising a linear carbon-based chain comprising at least one sequence of at least three covalent carbon-carbon double bonds, so as to enable delocalization of the electrons of the double bonds when the fluorophore is excited by light radiation so as to fluoresce in a range of wavelengths of between 700 nm and 1000 nm,
- a targeting assembly comprising at least two identical targeting molecules, and
- a cyclic oligopeptide:
  - configured so as to define a mean plane defining a first upper face and a second lower face,
  - comprising at least one lysine amino acid residue on the second lower face,
  - targeting molecules being fixed to the first upper face of the mean plane,
  - the fluorophore being fixed to the second lower face of the mean plane via a spacer arm connecting a carbon of the sequence of the at least three double bonds and a lysine amino acid residue of the oligopeptide,
  - the process comprises a step of fixing the fluorophore to the cyclic oligopeptide via the spacer arm prior to a step of fixing the targeting molecules to the oligopeptide.

LIST OF FIGURES

Figure 5A:
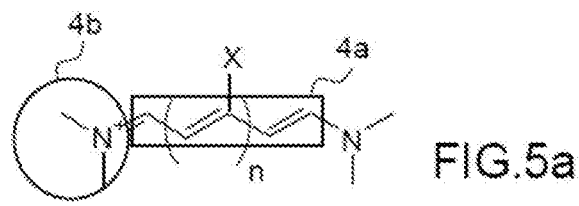
Figure 5B:
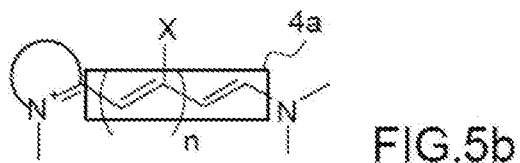
Figure 5C:
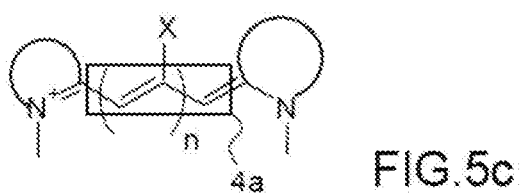
Figure 4:
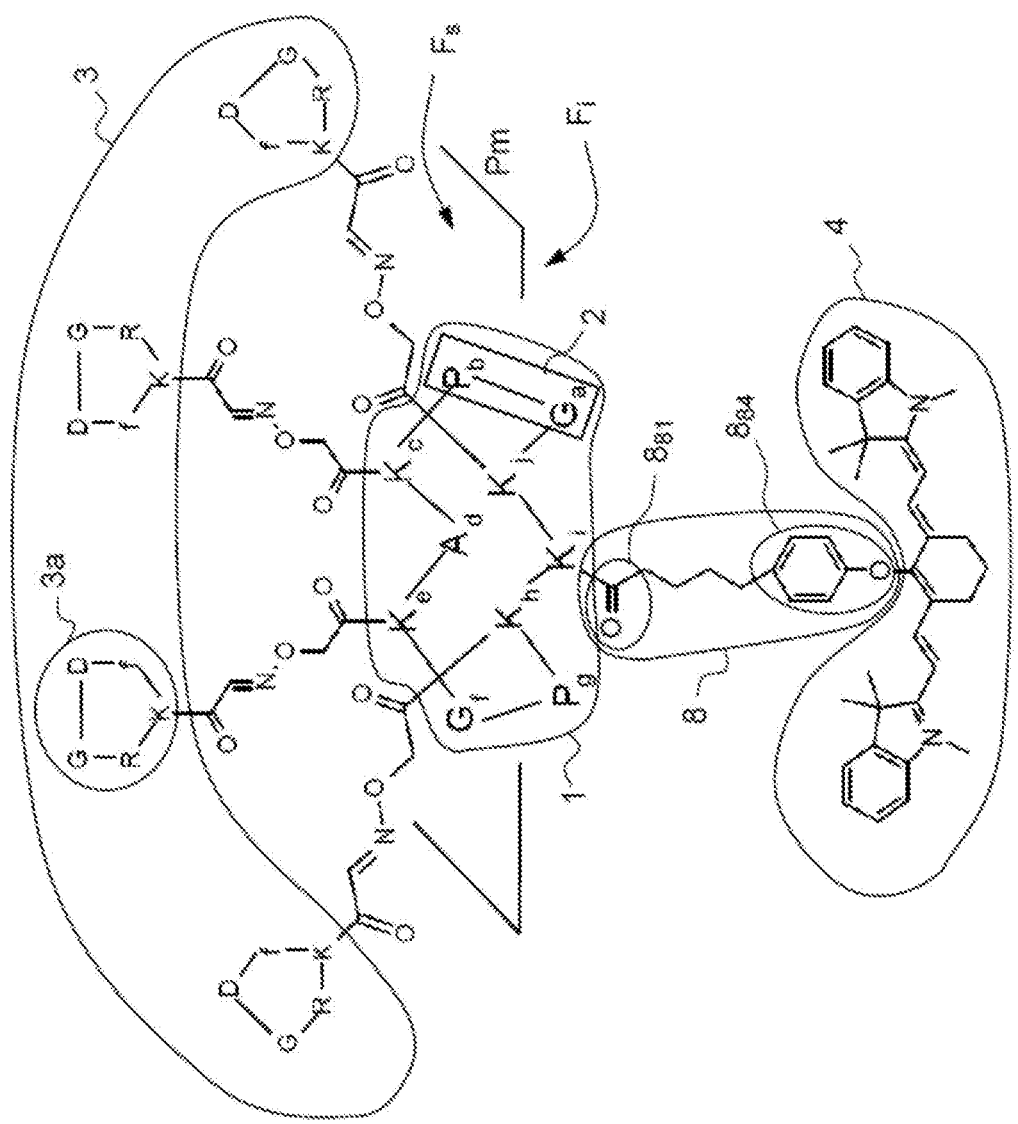
Figure 6A:
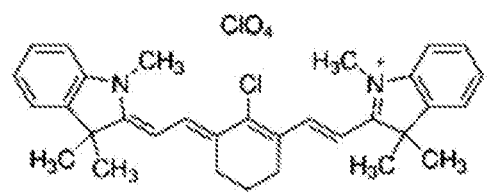
Figure 6B:
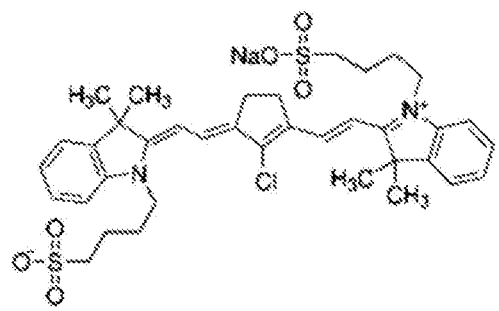
Figure 6C:
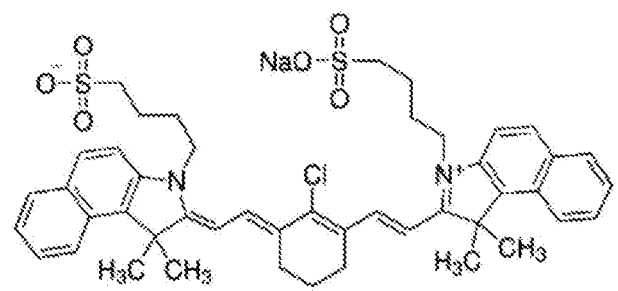
Figure 6D:
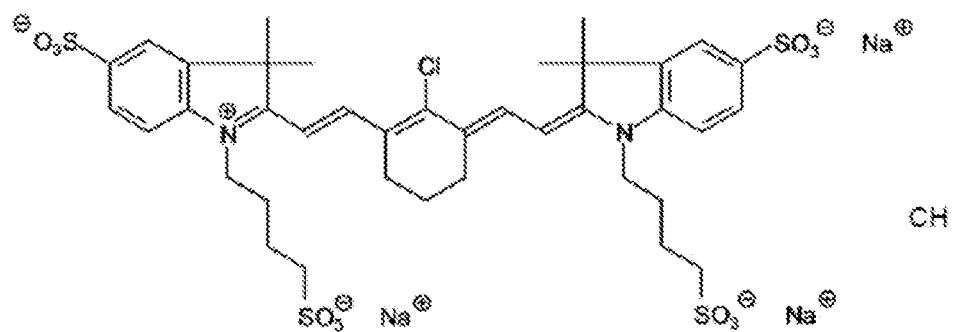
Figure 6E:
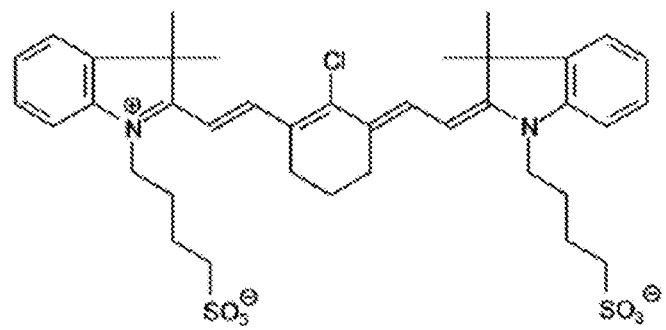
Figure 6F:
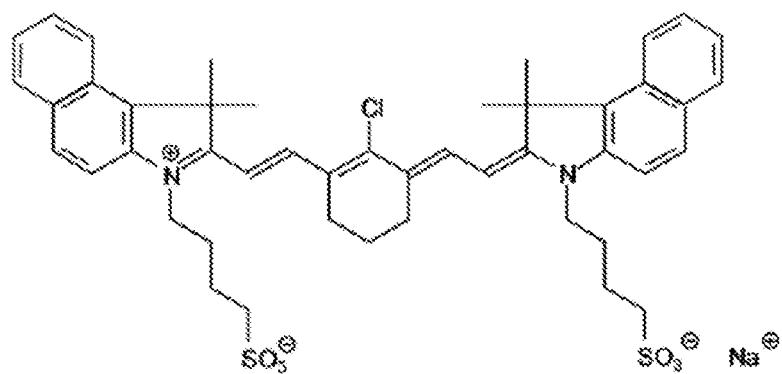
Figure 6G:
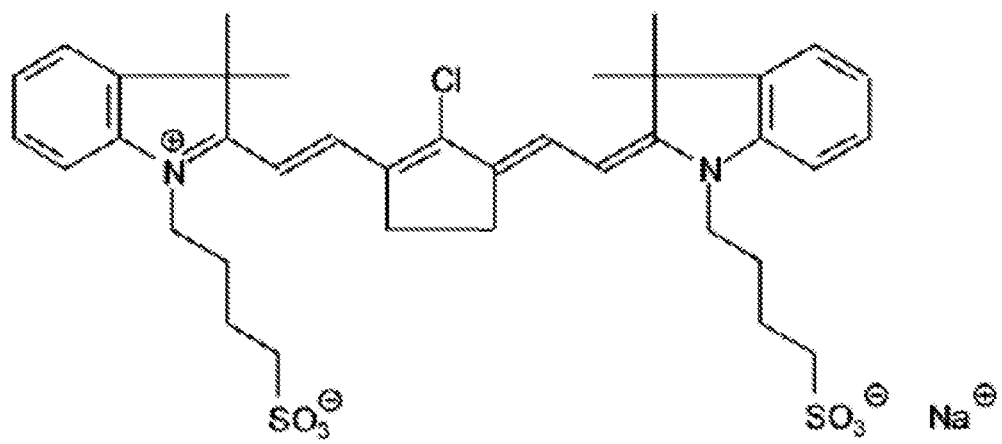
Figure 6H:
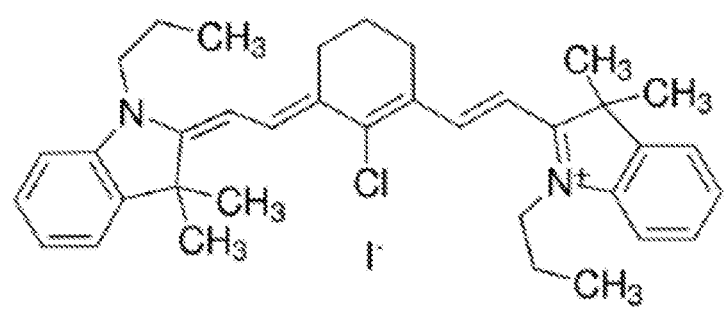
Figure 7A:
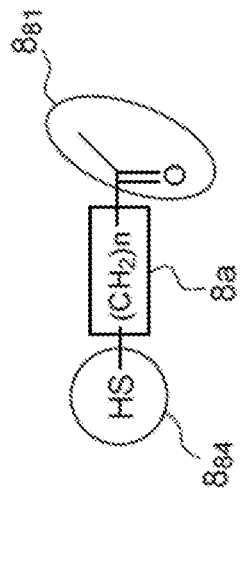
Figure 7B:
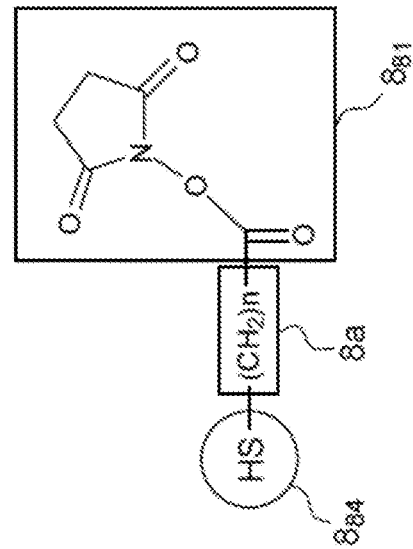
Figure 7C:
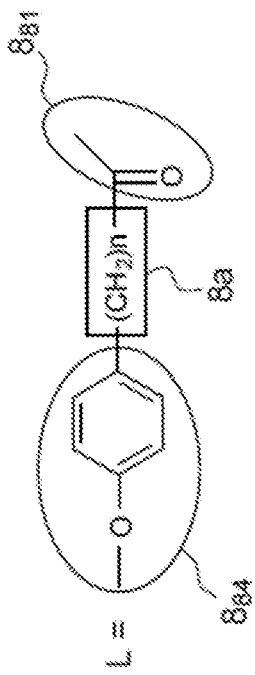
Figure 7D:
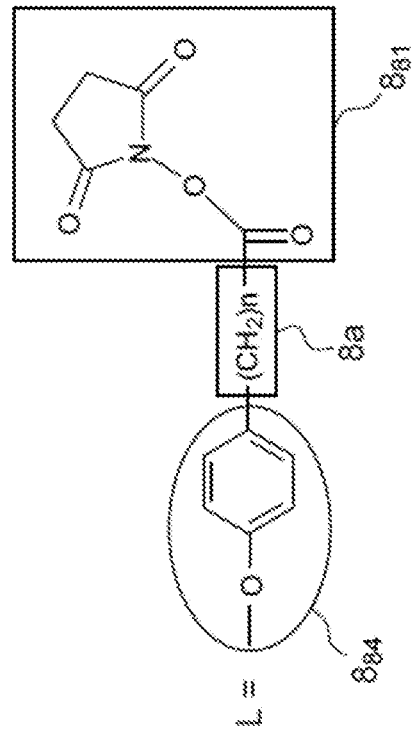
Figure 8:
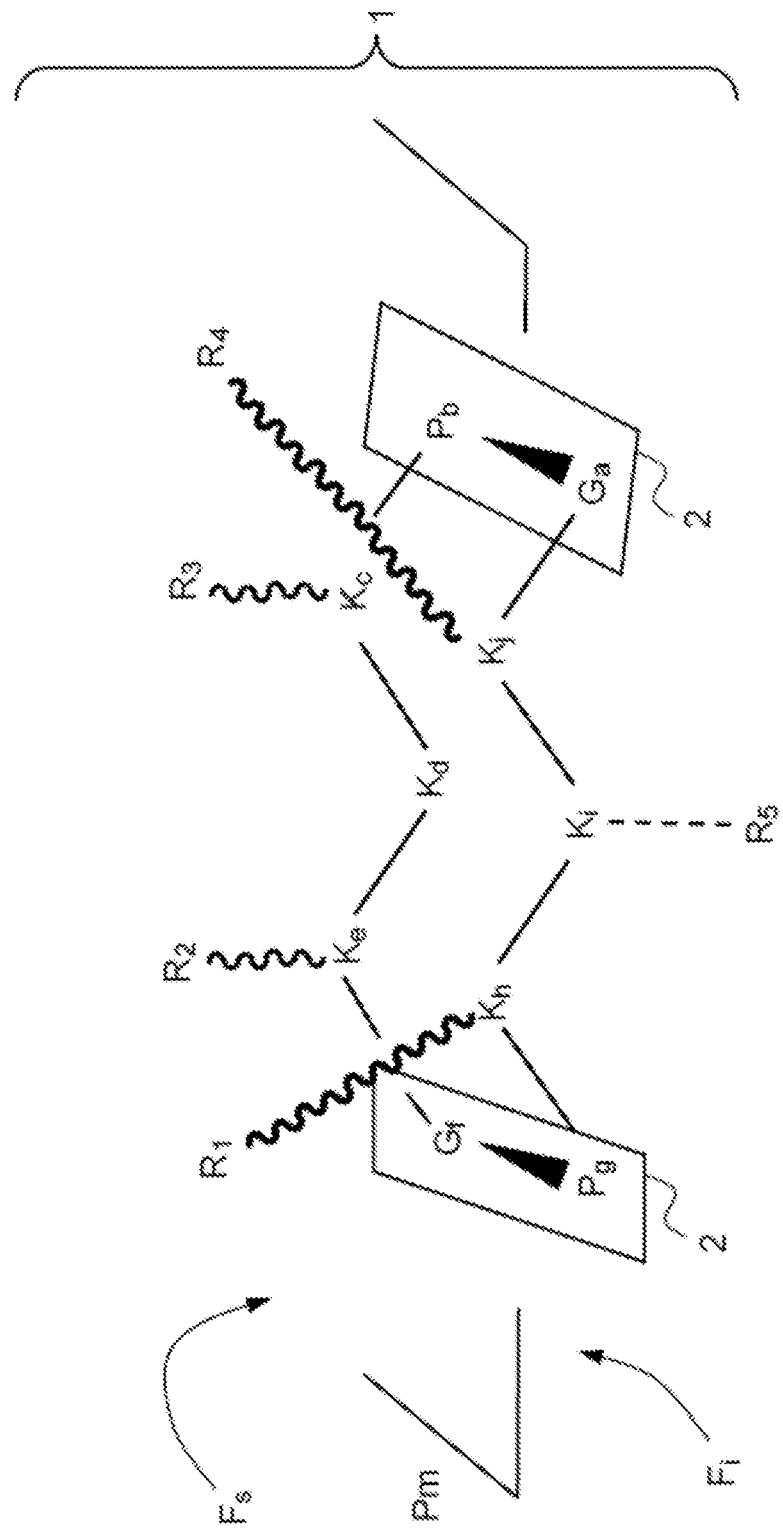
Figure 9:
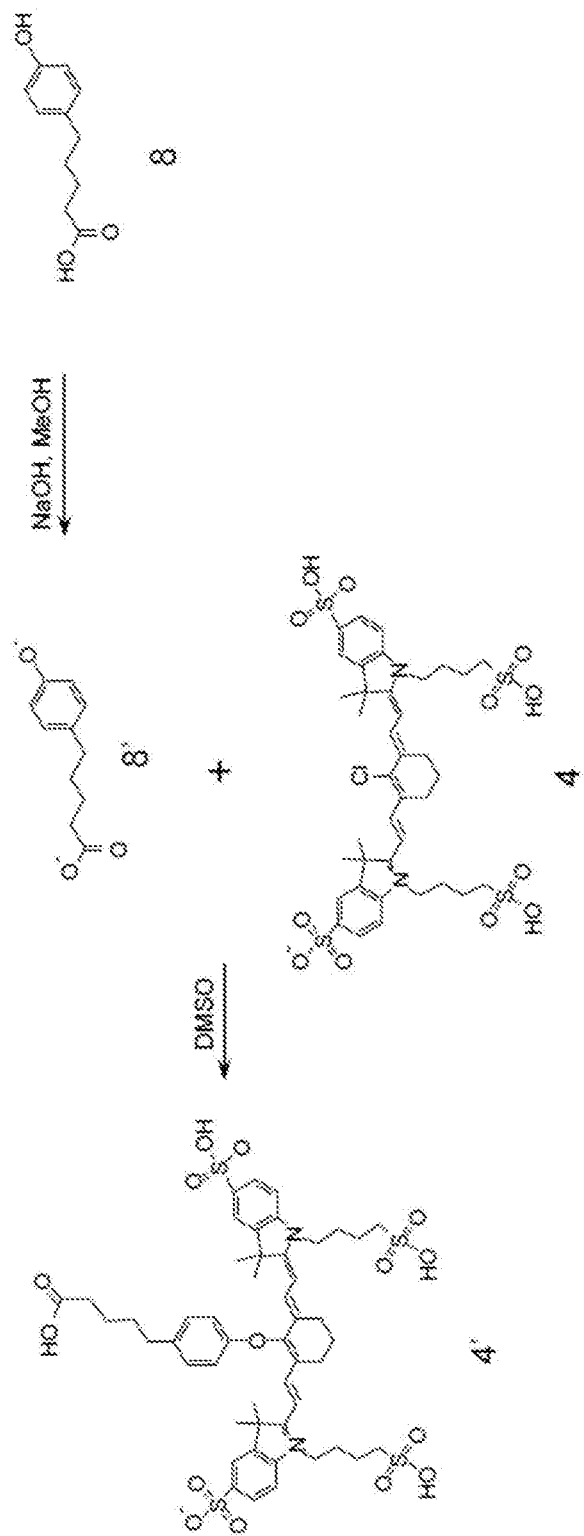
Figure 10A:
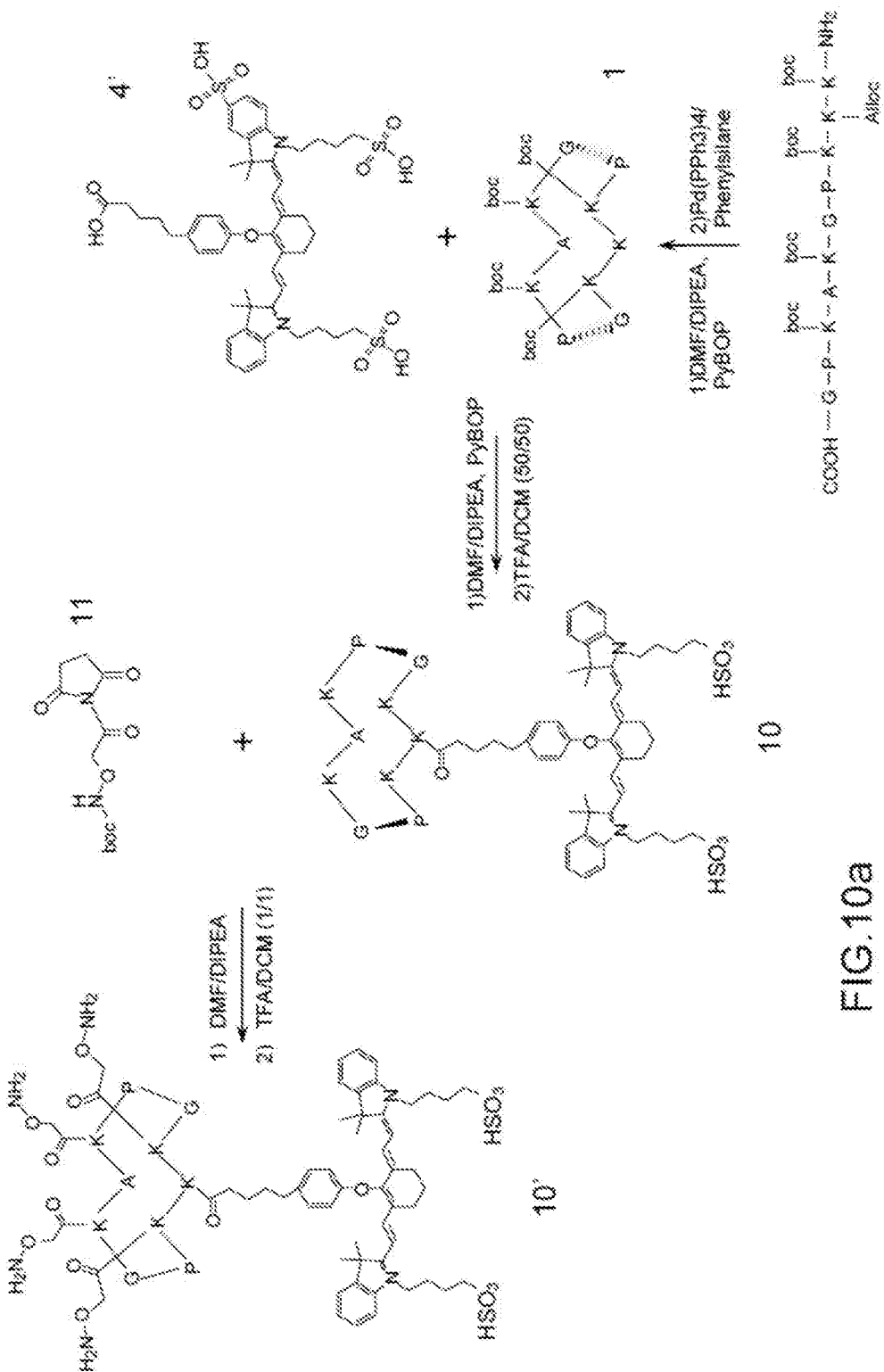
Figure 10B:
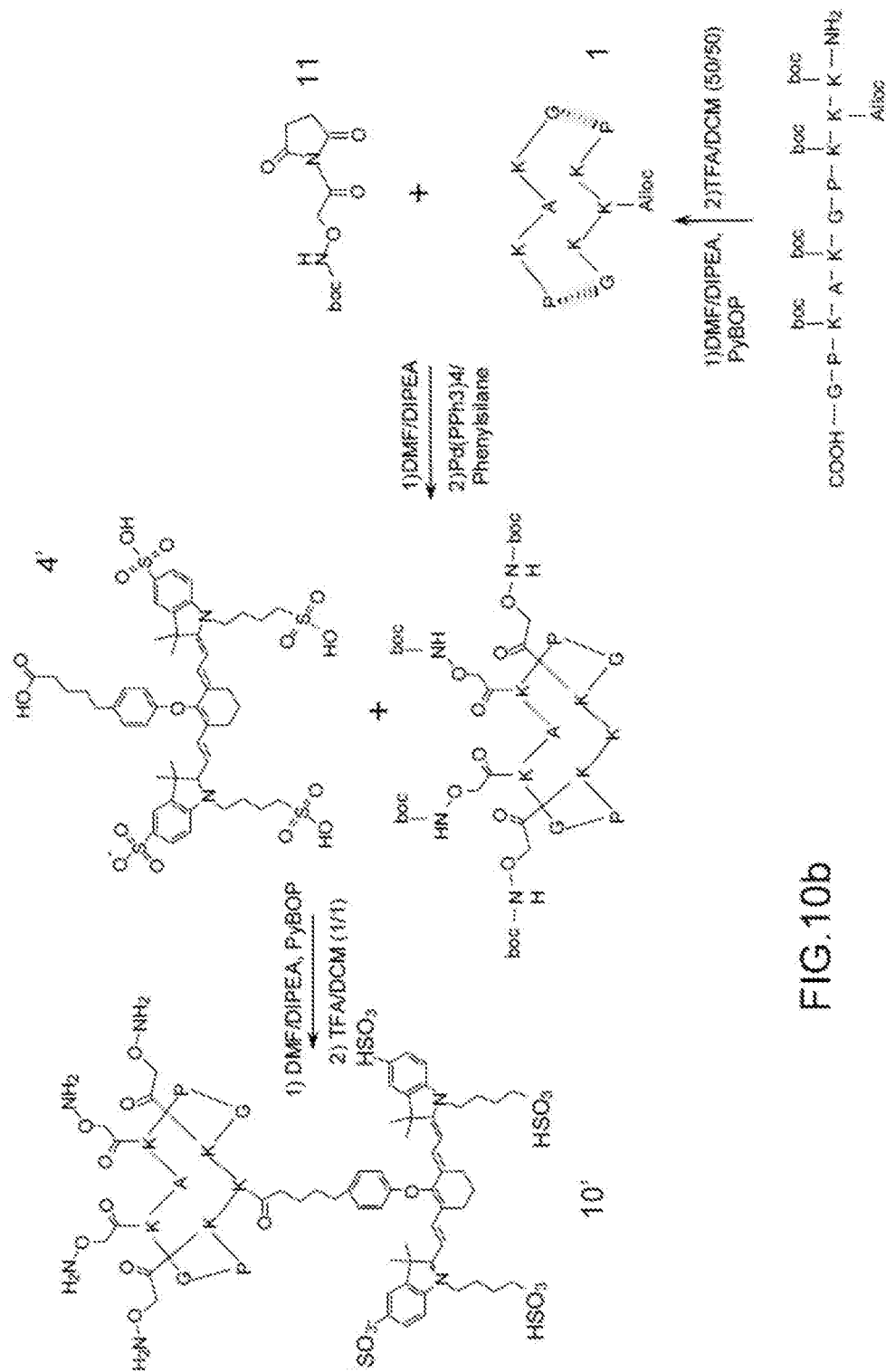
Figure 11:
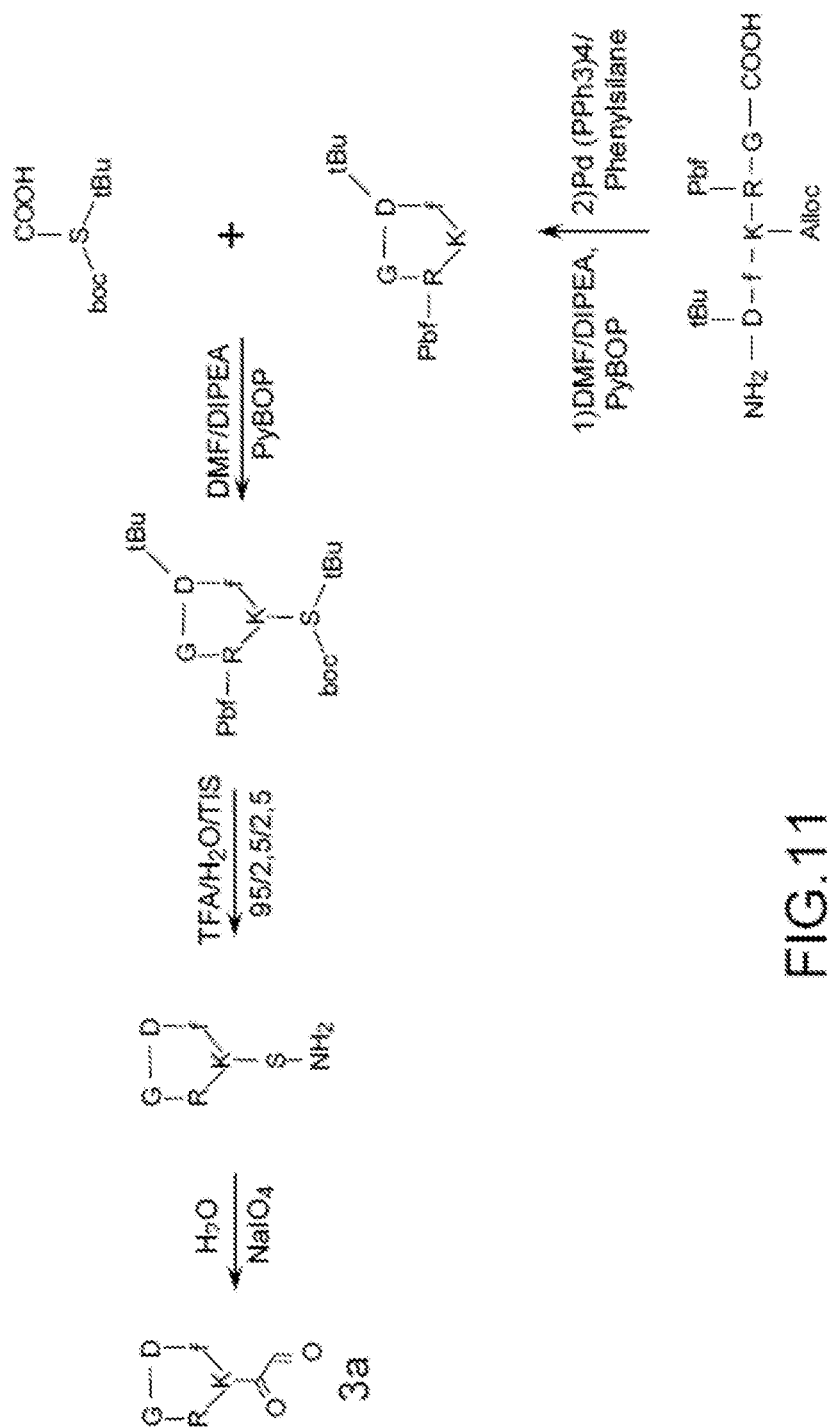
Figure 12:
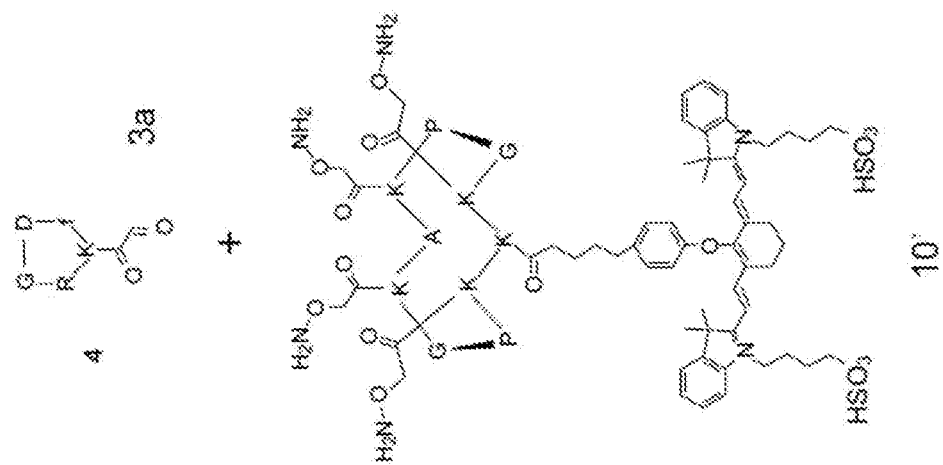
Figure 12:
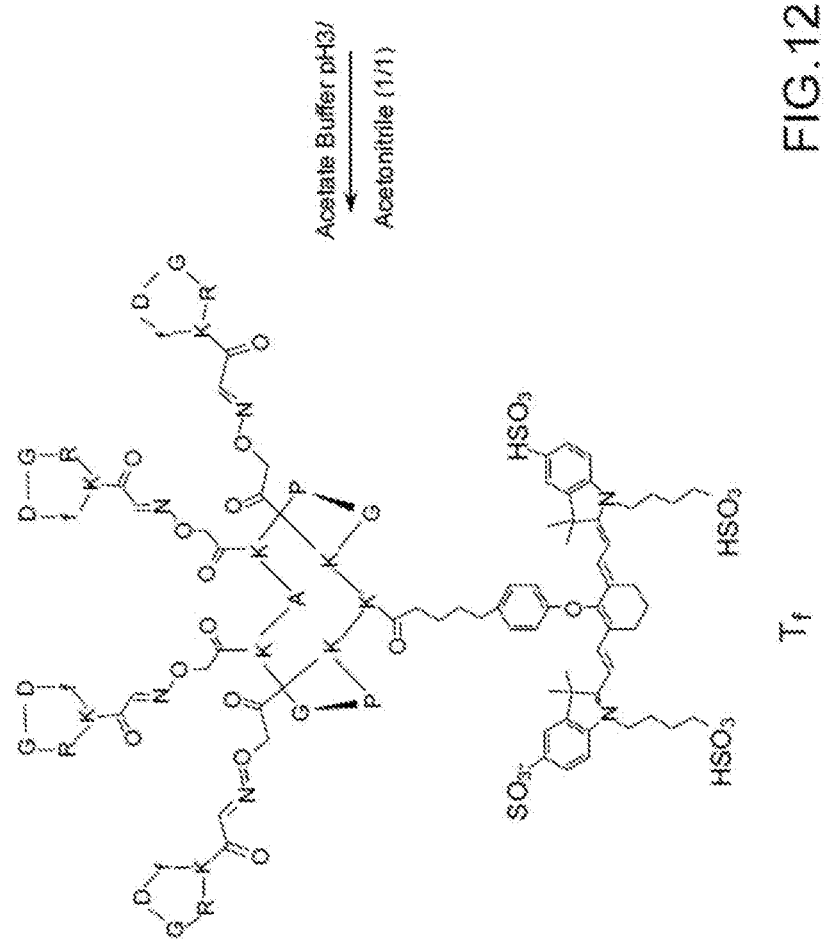
Figure 13A:
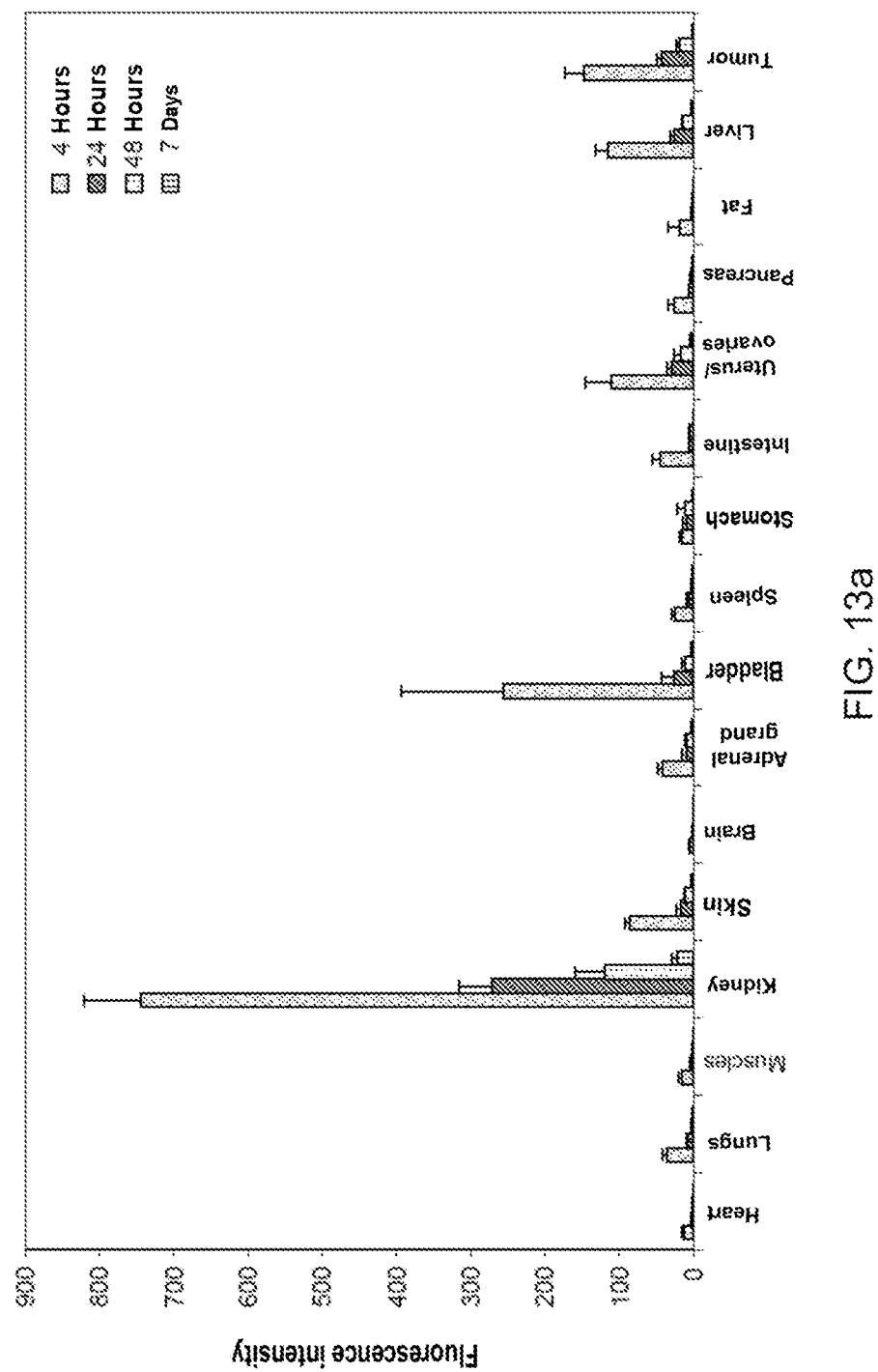
Figure 13B:
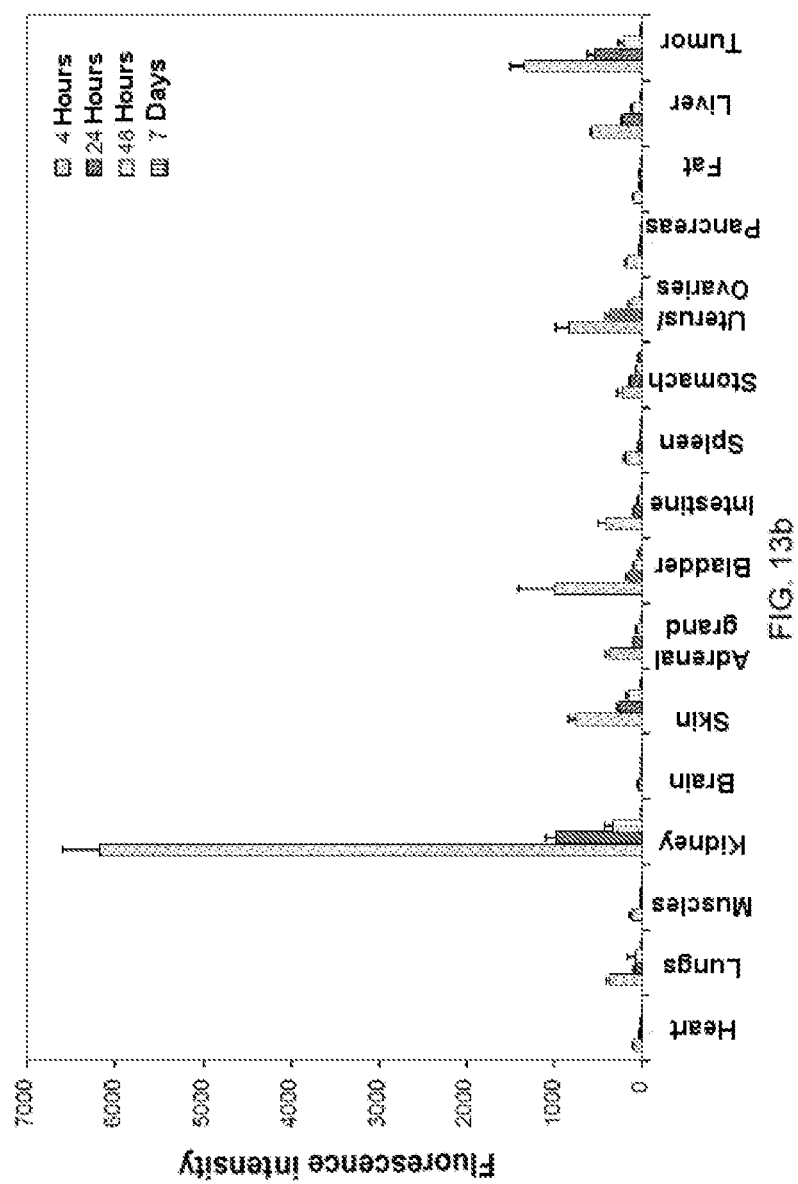

The invention will be better understood and other advantages will become apparent on reading the following description, which is given by way of non-limiting example, and by virtue of the appended figures in which:

FIG. 1, already described, represents a RAFT template,

FIG. 2, already described, illustrates a targeting molecule comprising a cyclic pentapeptide [-RGDfK-] specific for the $\alpha_v\beta_3$ integrin, FIG. 3, already described, represents a fluorescent tracer according to the known art, FIG. 4 illustrates a representative of the family of fluorescent tracers according to the invention, FIGS. 5a, 5b, and 5c represent the general formulae of fluorophores used in a tracer according to the invention, FIGS. 6a, 6b, 6c, 6d, 6e, 6f, 6g, and 6h represent examples of chemical formulae of commercial fluorophores which are potentially of use according to the invention, FIGS. 7a, 7b, 7c and 7d represent spacer arms used in a tracer according to the invention, FIG. 8 represents a RAFT template enabling the grafting of two fluorophores to the lower face Fi, FIG. 9 represents the coupling reactions between a spacer arm and a fluorophore according to the invention, FIGS. 10a and 10b represent the reactions for synthesizing the RAFT template, and for coupling between the fluorophore provided with the spacer arm and the RAFT template, according to the invention, FIG. 11 represents the reactions for synthesizing the targeting molecule according to the invention, FIG. 12 represents the coupling reaction between the fluorescent RAFT template and the targeting molecules via an amide bond, according to the invention;

FIG. 13a illustrates the tissue distribution of a tracer Tf according to the known art and FIG. 13b illustrates the tissue distribution of a tracer Tf according to an embodiment of the invention.

DETAILED DESCRIPTION

FIG. 4 is a semi-expanded formula of a representative of the fluorescent tracer Tf family according to the invention.

In the case in point, the fluorescent tracer Tf comprises a RAFT template 1 comprising, as in the document by Boturyn, a sequence of ten amino acid residues [K-K-K-P-G-K-A-K-P-G-] in cyclic form. The sequences of the amino acid residues [-Glycine-Proline] form bends 2 so as to define a mean plane Pm, on either side of which a fluorophore 4 and a targeting assembly 3 may be fixed. Generally, the targeting molecules 3 may be molecules for targeting tumors. These molecules may be peptides, and more particularly peptides able to target at least one integrin, preferentially $\alpha_v\beta_3$.

In the case in point, the targeting assembly 3 comprises cyclic pentapeptide molecules 3a comprising a specific sequence of RGD type. The cyclic pentapeptides 3a are connected to the RAFT template 1 at the lysine residues $K_c$, $K_e$, $K_h$, and $K_i$ of the upper face $F_s$ of the RAFT template 1. In the case in point, they are connected via an oxime bond, enabling good stability in vivo and in vitro. Nonetheless, it is also possible to connect them via an amide bond. Alternatively, it is possible to connect at least one targeting molecule 3a via a thioether bond, with the proviso that a lysine residue is replaced by a cysteine residue, in which case it is possible to graft one type of targeting molecules onto the lysine residues and another type of molecule onto the cysteine residue, thereby enabling the regioselective grafting of targeting molecules.

The fluorophore 4 is fixed to the template 1 via a spacer arm 8. In the case in point, the fluorophore 4 is IR775 (registered trademark) or 2-[(E)-2-{(3E)-2-chloro-3-[(2Z)-2-(1,3,3-trimethyl-1,3-dihydro-2H-indol-2-ylidene)ethylidene]cyclohex-1-en-1-yl}ethenyl]-1,3,3-trimethyl-3H-indolium chloride, depending on the nomenclature.

The spacer arm 8 comprises a sequence of five carbons, a phenolate function at one end $8_{84}$ of the carbon-based chain connecting the spacer arm 8 to the fluorophore 4 and a carboxylic function $8_{81}$ connecting the spacer arm 8 to the RAFT template 1.

More specifically, FIGS. 5a, 5b and 5c represent general formulae of fluorophores 4 potentially of use according to the invention.

The fluorophore 4 according to the invention must have properties of absorption in the near-infrared wavelength range of between 750 nm and 1000 nm and an emission peak having a maximum of between 770 nm and 870 nm. The fluorophore 4 also has a linear or non-linear carbon-based chain comprising a sequence of conjugated covalent double bonds, the electrons of the double bonds being able to delocalize. Moreover, the fluorophore 4 has, on one of the carbons of the carbon-based chain, a halogen group X which may react with a group.

FIG. 5a presents a fluorophore 4 comprising a linear carbon chain 4a having conjugated double bonds, the electrons of the double bonds being able to delocalize over the whole of the carbon-based chain 4a. The ends of the carbon-based chain 4a have tertiary amine and quaternary ammonium groups.

FIG. 5b also presents a fluorophore 4 potentially of use for producing a fluorescent tracer according to the invention. FIG. 5b differs from FIG. 5a in that the quaternary ammonium end has an aromatic group. FIG. 5c has, at each end of the carbon-based chain 4a, an aromatic group.

The aromatic group, such as pyrrole or indole, optionally comprises an aliphatic group having a functional group which is able to modify the physicochemical characteristics of the fluorescent tracer Tf. For example, the addition of a sulfonate group may increase hydrophilicity and thereby increase the solubility of the fluorescent tracer Tf in an aqueous solvent.

A number of examples of commercial fluorophores which are potentially of use are represented in FIG. 6:

IR786 (registered trademark), or 2-(2-[2-Chloro-3-([1,3-dihydro-1,3,3-trimethyl-2H-indol-2-ylidene]ethylidene)-1-cyclohexen-1-yl]ethenyl)-1,3,3-trimethylindolium perchlorate (FIG. 6a), IR806 (registered trademark) or internal salt (sodium salt) of 2-[2-[2-Chloro-3-[[1,3-dihydro-1,1-dimethyl-3-(4-sulfobutyl)-2H-benzo[e]indol-2-ylidene]-ethylidene]-1-cyclohexen-1-yl]-ethenyl]-1,1-dimethyl-3-(4-sulfobutyl)-1H-benzo[e]indolium hydroxide (FIG. 6b), IR820 (registered trademark) or internal salt (sodium salt) of 2-[2-[2-Chloro-3-[[1,3-dihydro-1,1-dimethyl-3-(4-sulfobutyl)-2H-benzo[e]indol-2-ylidene]-ethylidene]-1-cyclohexen-1-yl]-ethenyl]-1,1-dimethyl-3-(4-sulfobutyl)-1H-benzo[e]indolium hydroxide (FIG. 6c), S0456 (registered trademark) or internal salt (trisodium salt) of 3,3-Dimethyl-2-[2-[2-chloro-3-[2-[1,3-dihydro-3,3-dimethyl-5-sulfo-1-(4-sulfobutyl)-2H-indol-2-ylidene]-ethylidene]-1-cyclohexen-1-yl]-ethenyl]-5-sulfo-1-(4-sulfobutyl)-3H-indolium hydroxide (FIG. 6d), S2180 (registered trademark) or internal salt (trisodium salt) of 2-[2-(2-Chloro-3-[2-[1,1-dimethyl-7-sulfo-3-(4-sulfobutyl)-1,3-dihydro-benzo[e]indol-2-ylidene]-ethylidene]-cyclohex-1-enyl)-vinyl]-1,1-dimethyl-7-sulfo-3-(4-sulfobutyl)-1H-benzo[e]indolium hydroxide (FIG. 6e), S0306 (registered trademark) or internal salt (sodium salt) of 2-[2-[2-Chloro-3-[[1,3-dihydro-1,1-dimethyl-3-(4-sulfobutyl)-2H-benzo[e]indol-2-ylidene]-ethylidene]-1-cyclohexen-1-yl]-ethenyl]-1,1-dimethyl-3-(4-sulfobutyl)-1H-benzo[e]indolium hydroxide (FIG. 6f), S0121 (registered trademark) or internal salt (sodium salt) of 2-[2-[2-Chloro-3-[2-[1,3-dihydro-3,3-dimethyl-1-(4-sulfobutyl)-2H-indol-2-ylidene]-ethylidene]-1-cyclohexen-1-yl]-ethenyl]-3,3-dimethyl-1-(4-sulfobutyl)-3H-indolium hydroxide (FIG. 6g), IR780 iodide (registered trademark) or 2-[2-[2-Chloro-3-[(1,3-dihydro-3,3-dimethyl-1-propyl-2H-indol-2-ylidene)ethylidene]-1-cyclohexen-1-yl]ethenyl]-3,3-dimethyl-1-propylindolium iodide (FIG. 6h).

These fluorophores have a much lower cost than the fluorophores used for synthesizing fluorescent tracers Tf according to the prior art.

The difference in cost may be explained on the one hand by the fact that these fluorophores are structurally simpler than the fluorophores used formerly, of IRDye® 800 type, and one the other hand by the fact that it is not necessary to activate them.

Moreover, FIGS. 7a, 7b, 7c and 7d present semi-expanded formulae of spacer arms 8 which are potentially of use.

Generally, the spacer arm 8 according to the invention comprises a carbon-based chain 8a, a first end group $8_{84}$ connecting the fluorophore 4 to the spacer arm 8 and a second end group $8_{81}$ connecting the spacer arm 8 to the RAFT template 1.

Although the prior art presents a spacer arm consisting of a tyrosine, it has been demonstrated that it is not possible to graft a fluorophore 4 onto a RAFT template 1 according to the invention via a spacer arm consisting of a tyrosine residue, especially because of steric hindrance or spacing problems.

Preferentially, the number of carbons of the carbon-based chain 8a is greater than or equal to 4, thereby facilitating the grafting of the fluorophore 4 and thereby limiting the problems associated with steric hindrance.

The first end group $8_{84}$ may be an amide group (corresponding to an amine group before a reaction between the spacer arm 8 and the fluorophore 4), an ether group (corresponding to an alcohol group before a reaction between the spacer arm 8 and the fluorophore 4) or a thioether group (corresponding to a thiol group before a reaction between the spacer arm 8 and the fluorophore 4). The fixing of the spacer arm 8 via the first end group $8_{84}$ substantially modifies the emission maximum. Indeed, an amine first end group reduces the wavelength of the maximum fluorescence peak by 100 to 150 nm. Thus, this type of first end group will not be favored. An ether first end group (FIGS. 7a and 7c, corresponding to an alcohol group before a reaction between the spacer arm 8 and the fluorophore 4) reduces the wavelength of the emission peak maximum by 10 to 15 nm. A thioether first end group (FIGS. 7b and 7d, corresponding to a thiol group before a reaction between the spacer arm 8 and the fluorophore 4) increases the wavelength of the emission peak maximum by 10 to 15 nm. In addition, the use of a first end group of phenol type (FIG. 7a and FIG. 7c) increases delocalization of the electrons of the carbon-based chain 4a of the fluorophore, which increases the quantum yield. Generally, an end group $8_{84}$ of the spacer arm is able to increase delocalization of the electrons of the carbon-based chain 4a of the fluorophore 4, and thereby to increase the quantum yield.

The second end group $8_{81}$ may be a carboxylic acid (FIG. 7a and FIG. 7b) or succinimide ester (FIG. 7c and FIG. 7d).

The spacer arm 8 is fixed, via the second end group $8_{81}$, to a lysine residue on what is referred to as the lower face $F_i$ of the RAFT template 1.

According to a variant of the invention represented in FIG. 8, the alanine residue located on what is referred to as the lower face $F_i$ of the RAFT template 1 may be substituted by a lysine residue, in which case a second fluorophore may additionally be fixed so as to enable FRET fluorescence, for example.

According to another aspect of the invention, a process is proposed for producing the tracer Tf comprising a step of coupling the fluorophore 4 with the RAFT template 1 so as to form a fluorescent RAFT template prior to the step of coupling the targeting molecules 3.

This production process reduces starting material losses, and more particularly losses of the targeting molecules, and makes it possible to avoid the step of activating the fluorophore before the coupling step.

The process comprises:

- a first step, illustrated in FIG. 9, for preparing a modified fluorophore 4' in which the spacer arm 8 is coupled to the fluorophore 4,
- a second step, represented in FIG. 10, in which the RAFT template 1 is synthesized,
- a third step, represented in FIG. 10, in which the RAFT template 1 is coupled to the modified fluorophore 4' so as to form a fluorescent template 10,
- a fourth step, illustrated in FIG. 10, in which an oxime bond precursor 11 is grafted onto the RAFT template 1 on the lysine residues of what is referred to as the upper face $F_s$ so as to form a modified fluorescent template 10',
- a fifth step, represented in FIG. 11, in which the targeting molecules 3a are synthesized, and
- a sixth step, illustrated in FIG. 12, for coupling between the targeting molecules 3a and the modified fluorescent template 10'.

More specifically, FIG. 9 presents the steps for preparing the modified fluorophore 4', described especially in the document by Hyun, H. et al., "c-GMP-compatible preparative scale of near-infrared fluorophores. Contrast Media Mol. Imaging, 2012, 7: 516". The spacer arm 8, 5-(4-hydroxyphenyl)pentanoic acid, comprises a first phenol end group $8_{81}$. The phenol is converted to phenolate, which is more reactive than phenol, in a solution of sodium hydroxide in methanol, to form a modified spacer arm 8'. The spacer arm 8' obtained is then mixed with the fluorophore 4, in this case S0456 (or internal salt (trisodium salt) of 3,3-Dimethyl-2-[2-[2-chloro-3-[2-[1,3-dihydro-3,3-dimethyl-5-sulfo-1-(4-sulfobutyl)-2H-indol-2-ylidene]-ethylidene]-1-cyclohexen-1-yl]-ethenyl]-5-sulfo-1-(4-sulfobutyl)-3H-indolium hydroxide) in DMSO (acronym for DiMethyl SulfOxide) to obtain the modified fluorophore 4' consisting of the fluorophore 4 onto which the spacer arm 8' is grafted.

FIG. 10a presents the second, third and fourth sub-steps of the process. Firstly, a linear decapeptide comprising the sequence of amino acid residues [K(Boc)-K(Alloc)-K(Boc)-P-G-K(Boc)-A-K(Boc)-P-G-] is synthesized on resin, the Boc and Alloc groups being protecting groups so as to subsequently enable regioselective functionalization of the fluorescent template. After detachment from the resin, the decapeptide is cyclized and the lysine residue protected by the (Alloc) group is deprotected in the presence of palladium)(Pd$^0$) and phenylsilane so as to form a RAFT template 1 having a mean plane Pm. The modified fluorophore 4' is then grafted onto the deprotected lysine residue. The Boc protecting groups on the lysine residues of what is referred to as the upper face $F_s$ are cleaved in acid medium then a protected oxyamine precursor 11 is grafted onto the lysine residues via an amide bond, to form the modified fluorescent RAFT template 10'. It should be noted that the third step and the fourth step may be switched around, as illustrated in FIG. 10b. In the case in point, firstly the Boc protecting groups on the lysine residues of what is referred to as the upper face $F_s$ are cleaved in acid medium then protected oxyamine precursors 11 are grafted onto the lysine residues via an amide bond. The lysine residue located on the lower face $F_i$ protected by the (Alloc) group is deprotected so as to enable the grafting of the modified fluorophore 4' to form a modified fluorescent template 10'.

Moreover, it is interesting to note that the sub-step of activating the fluorophore 4, which is essential in the process according to the prior art, is not necessary in the process according to the invention. In the invention, the step of activating the fluorophore 4 carried out in the prior art is in part bypassed by a step of preparing a modified fluorophore 4' in which an arm 8 reacts with a halogen group X present on one of the carbons of the carbon-based chain. In this way, the spacer arm 8 connects a carbon of the sequence of the at least three double bonds of the fluorophore 4. This arrangement enables a reduction in the cost of synthesizing the tracer, with equivalent and/or better performance.

FIG. 13a illustrates the tissue distribution of a tracer Tf according to the known art, described in FIG. 3, at different times post-injection.

In the case in point, the fluorescence was measured at times post-injection of 4 h, 24 h, 48 h then seven days and the organs or tissues studied were: the heart, the lungs, the muscles, the kidney, the skin, the brain, the adrenal glands, the bladder, the spleen, the stomach, the intestines, the ovaries and the uterus, the pancreas, fat, the liver and a subcutaneous murine mammary tumor (Ts/Apc).

The diagram shows that the fluorescence intensity is greatest at a time, post-injection of the tracer Tf according to the known art, of 4 h, and decreases after 24 h. After seven days, the fluorescence intensity in the organs and tissues is virtually zero.

In addition, the diagram shows that the tracer Tf according to the known art is particularly well-suited for targeting a tumor which is overexpressing the $\alpha_v\beta_3$ integrin. This diagram also shows a significant accumulation of the tracer Tf according to the known art in the kidneys from 4 hours post-injection, demonstrating rapid renal elimination of the product.

FIG. 13b illustrates the tissue distribution of a tracer Tf according to an embodiment of the invention. FIG. 13b illustrates in particular the fluorescence intensity of a tracer Tf according to an embodiment of the invention, for example illustrated in FIG. 4, in the same organs and tissues as those studied in FIG. 13a.

The tissue distribution of the tracer Tf according to the invention is similar to the distribution observed for the tracer Tf according to the known art.

Moreover, the affinity of the tracer Tf according to the invention is similar to the affinity of a tracer Tf according to the known art, such as Cy5-RAFT-(c[RGDfK])$_4$. This is explained by the fact that the targeting molecules are identical and represented in identical amounts in the tracer Tf according to the known art and the tracer Tf according to the invention.

On the other hand, the tracer Tf according to the invention has a much greater affinity than a monomeric tracer having the targeting molecule represented in a single example.

FIGS. 13a and 13b illustrate similar, equivalent and/or superior performance of a tracer Tf according to an embodiment of the invention compared to a trace Tf according to the known art.

FIG. 11 presents the steps for synthesizing the targeting molecule 3a. Firstly, the linear pentapeptide comprising the sequence of amino acid residues RGD specific for integrins is synthesized on a resin. In the case in point, the pentapeptide comprises the sequence [-D(tBu)-f-K(Alloc)-R(Pbf)G-]. After detaching the peptide from the resin, said peptide is cyclized then the lysine residue protected by the Alloc group is subsequently deprotected in the presence of palladium)(Pd$^0$) and phenylsilane. A protected serine residue is the grafted onto the lysine residue before total deprotection of the pentapeptide in acid medium. The alcohol function of the serine is then oxidized with sodium periodate in water, to obtain an aldehyde group.

FIG. 12 illustrates the step of coupling between the modified fluorescent template 10' and the cyclic pentapeptides 3a.

In the claimed process, the commercial fluorophore 4 is involved very early on in the process for synthesizing the fluorescent tracer Tf compared to the process of the prior art.

The requirements for purity and quality relating to starting materials incorporated into formulations intended for human administration involved early on in the synthesis process are less stringent than for starting materials involved at the end of the process, as is the case in the process of the prior art. In the case in point, the fluorophore 4 may therefore be of lesser quality and purity than those required during the synthesis according to the process of the prior art, which contributes significantly to lowering the purchase cost of the fluorophore 4.

Moreover, unlike the process described in the prior art, the step of activating the fluorophore prior to the step of coupling between the modified fluorophore 10' and the RAFT template 1 is not necessary, which makes it possible to further reduce the costs of producing the fluorescent tracer Tf according to the invention.

Thus, the synthesis of 15 g of fluorescent tracer Tf requires 30 g of RAFT, 105 g of RGD and 13 g of fluorophore.

The novel family of fluorescent tracers proposed in the present invention makes it possible to significantly reduce costs, on the one hand, by enabling the use of less expensive materials, but also by improving the production process, thereby making it possible to do away with reaction steps.

The invention claimed is:

1. A fluorescent tracer for targeting tumors, comprising:
   a fluorophore chosen from the following fluorophores: S0121, S0306, S0456, S2180, IR775 chloride, IR780 iodide, IR786, IR806, IR820;
   an assembly for targeting $\alpha_v\beta 3$ integrin consisting of 4 targeting molecules being cyclic pentapeptides of sequence [RGDfK]; and
   a cyclic decapeptide comprising the following sequence of amino acid residues: [-$G_a$-$P_b$-$K_c$-$A_d$-$K_e$-$G_f$-$P_g$-$K_h$-$K_i$-$K_j$-], the cyclic decapeptide being configured to define a mean plane defining a first upper face consisting of the four lysine residues $K_c$, $K_e$, $K_h$ and $K_j$, and a second lower face consisting of the residues $G_a$, $P_b$, $A_d$, $G_f$, $P_g$ and $K_i$,
   each of the targeting molecules being fixed to a different lysine amino acid residue of the four lysine residues $K_c$, $K_e$, $K_h$ and $K_j$ via oxime bonds,
   the fluorophore being fixed to the second lower face of the mean plane via a spacer arm being 5-(4-hydroxyphenyl)pentanoic acid,
   the spacer arm being fixed to the fluorophore via an ether bond resulting from the reaction between the phenol function of the spacer arm and the chlorine element of the fluorophore and the spacer arm being fixed to the lysine residue $K_i$ via an amide bond.

2. A process for synthesizing a fluorescent tracer for targeting tumors of claim 1 comprising:
   (i) preparation of a modified fluorophore in which the spacer arm is coupled to the fluorophore, wherein fluorophore is selected from the group consisting of S0121, S0306, S0456, S2180, IR775 chloride, IR780 iodide, IR786, IR806 and IR820;
   (ii) preparation of a regioselectively addressable functionalized (RAFT) template, wherein RAFT is a cyclic decapeptide represented by sequence of amino acid residues: $G_a$-$P_b$-$K_c$-$A_d$-$K_e$-$G_f$-$P_g$-$K_h$-$K_i$-$K_j$;
   (iii) coupling of RAFT template to the modified fluorophore to form a fluorescent template;
   (iv) grafting an oxime bond precursor onto the RAFT template on the lysine residues to form a modified fluorescent template;
   (v) synthesis of targeting molecules; and
   (vi) coupling between the targeting molecules and the modified fluorescent template.

* * * * *